(12) United States Patent
Schmitt et al.

(10) Patent No.: US 7,991,464 B2
(45) Date of Patent: Aug. 2, 2011

(54) TRANSDERMAL THERAPEUTIC SYSTEM

(75) Inventors: Katrin Schmitt, Freiburg (DE); Christian Hoffmann, Freiburg (DE)

(73) Assignee: Fraunhofer-Gesellschaft zur Foerderung der Angewandten Forschung E.V., Munich (DE)

( * ) Notice: Subject to any disclaimer, the term of this patent is extended or adjusted under 35 U.S.C. 154(b) by 73 days.

(21) Appl. No.: 12/301,211

(22) PCT Filed: Apr. 5, 2007

(86) PCT No.: PCT/EP2007/003125
§ 371 (c)(1),
(2), (4) Date: Mar. 31, 2009

(87) PCT Pub. No.: WO2007/131577
PCT Pub. Date: Nov. 22, 2007

(65) Prior Publication Data
US 2009/0208561 A1 Aug. 20, 2009

(30) Foreign Application Priority Data
May 17, 2006 (DE) .................. 10 2006 023 186

(51) Int. Cl.
*A61N 1/30* (2006.01)
(52) U.S. Cl. ......................................................... 604/20
(58) Field of Classification Search .............. 604/19–22, 604/890.1, 131, 500–522, 114
See application file for complete search history.

(56) References Cited

FOREIGN PATENT DOCUMENTS
DE 695 26 371 2/1997
WO WO-01/97899 12/2001

OTHER PUBLICATIONS
German Search Report.
Dermal and Transdermal Drug Delivery; By Gurny and Teubner.

*Primary Examiner* — Manuel A Mendez
(74) *Attorney, Agent, or Firm* — Bill C. Panagos; Rader, Fishman & Grauer PLLC

(57) ABSTRACT

The present invention relates to a transdermal therapeutic system for the controllable release of an active ingredient, particularly a substance promoting wound healing, to a chronic wound or for chemotherapy, with at least one waveguide, wherein the active ingredient is deposited on the waveguide via a bond that is cleavable by electromagnetic pulses in the waveguide.

26 Claims, 3 Drawing Sheets

TRANSDERMAL THERAPEUTIC SYSTEM

CROSS REFERENCE TO RELATED APPLICATIONS

This application claims priority based on German Patent Application 10 2006 023 186.4 filed May 17, 2006, and PCT application PCT/EP2007/003125 filed on Apr. 25, 2007, which are hereby incorporated by reference in their entireties.

TECHNICAL FIELD

The present invention relates to a transdermal therapeutic system which is particularly usable for treatment directly on a patient, for instance of chronic wounds, or in chemotherapy.

BACKGROUND

Transdermal systems constitute a form of medication for a patient, wherein an active ingredient, mostly provided on a plaster or patch, is absorbed for some time (often for several hours or days) through the patient's skin in the underlying vessels or the underlying tissue.

This form of medication makes it possible to bypass the first-pass metabolism, i.e. the first liver passage. This can reduce the required dosage of active ingredient. This helps to prevent overdosage that is stressful for organs and circulation.

A known transdermal therapeutic system is offered by "passive" patches, for instance fentanyl patches for tumor pain therapy or nicotine patches for enabling people to stop smoking. These "passive" patches are left on the skin for some time, e.g. up to 72 hours, thereby continuously releasing their active ingredient from an adhesive layer. The patch is then replaced.

Although the active ingredient can thereby be released through the skin continuously for some time, this release process cannot be actively controlled during application on the skin.

It is however advantageous to release the active ingredient in dosed form for a specific period of time because this will then permit an individual medication for the patient. Thus a controllable transdermal therapeutic system makes it possible to minimize the total amount of active ingredient released with the same therapeutic efficiency.

Such a controllable system is represented by electrochemically operating transdermal therapeutic systems in which the active ingredient is stored in an adhesive layer. With the help of two electrodes an electric field is applied to the adhesive layer. Owing to the action of the electric field applied the active ingredient is delivered in dosed form.

In this electrochemically operating release method, however, the respective active-ingredient molecule must carry a corresponding charge. Moreover, the delivered dose is predetermined by the value of the potential difference and by the duration of the electric field applied.

Moreover, all of the transdermal therapeutic systems that have so far been available are based on an immobilization of an active ingredient in an adhesive layer, which frequently causes contact allergies in the patients concerned, i.e. independently of the active ingredient itself.

SUMMARY

It is therefore an object of the present invention to provide an improved transdermal therapeutic system with controllable active-ingredient dosage.

According to the invention the present object is achieved with a transdermal therapeutic system for the controllable release of an active ingredient, with at least one waveguide, wherein the active ingredient is deposited on the waveguide via a bond that is cleavable by electromagnetic pulses in the waveguide.

With the transdermal therapeutic system according to the invention an optically controllable active-ingredient release and dosage are possible.

In the transdermal therapeutic system according to the invention the active ingredient to be released is immobilized on a surface of the waveguide by means of the cleavable bond. Due to an electromagnetic pulse in the waveguide and a corresponding cleavage of the retaining bond the active ingredient is released in a controlled way.

This enables the application of the active ingredient over time (dosage). The therapeutic efficiency can thereby be enhanced. Moreover, it is possible to reduce the costs, especially in cases where only small amounts of the active ingredient are to be used over a long period of time. Moreover, the transdermal therapeutic system according to the invention permits the broad use of active ingredient molecules because both charged and uncharged active ingredient molecules can be immobilized on the surface of the waveguide. In the transdermal therapeutic system according to the invention, an adhesive layer can also be dispensed with, whereby contact allergies to this adhesive layer are excluded.

Preferably, the waveguide is at least formed as a polymer fiber, particularly as a polymer fiber composite. Alternatively, the waveguide may be formed as a polymer layer, particularly as a planar carrier film, the polymer layer being here preferably permeable to air.

Furthermore, the waveguide may be configured as an optical waveguide, wherein preferably light in the visible or ultraviolet wavelength range or IR light is usable. When UV light is used, it is advantageous that the transdermal therapeutic system (particularly when formed as a wound bandage or patch or wound dressing) can also be exposed to visible light temporarily. Moreover, the UV light produces a simultaneous disinfecting effect on a skin surface, which offers a further advantage when the patch/wound bandage remains on the skin for a long time.

According to a further embodiment the cleavable bond is a photolabile linker which is cleavable through the action of an evanescent field, which is produced by light pulses in the optical waveguide. Here the light intensity in the evanescent field can be kept so low that even in cases where UV light is used, and despite disinfection of the skin surface, damage to the skin can be avoided at any rate.

The transdermal therapeutic system may also comprise an optically based control system for controlling the generation of the electromagnetic pulses for the dosed release of the active ingredient. To be more specific, a light source can be used for generating the light pulses, particularly a light-emitting diode in the UV range.

Furthermore, an optical device may be provided for coupling the electro-magnetic pulses into the waveguide.

Moreover, the transdermal therapeutic system is preferably divided into segments, the individual segments being activatable for the dosed release of the active ingredient.

According to a further preferred embodiment a sensor is provided for determining a dose of released active ingredient. This sensor may comprise a diode or a diode array for measuring extinction in dependence upon the surface covering density for determining the dose of released active ingredient.

Furthermore, the transdermal therapeutic system may comprise a carrier layer on which the waveguide is arranged. Said carrier layer may here be formed as a patch, wound dressing or wound bandage.

BRIEF DESCRIPTION OF THE DRAWINGS

The present invention shall be explained hereinafter with reference to preferred embodiments in connection with the associated drawings, in which.

Figure 1:
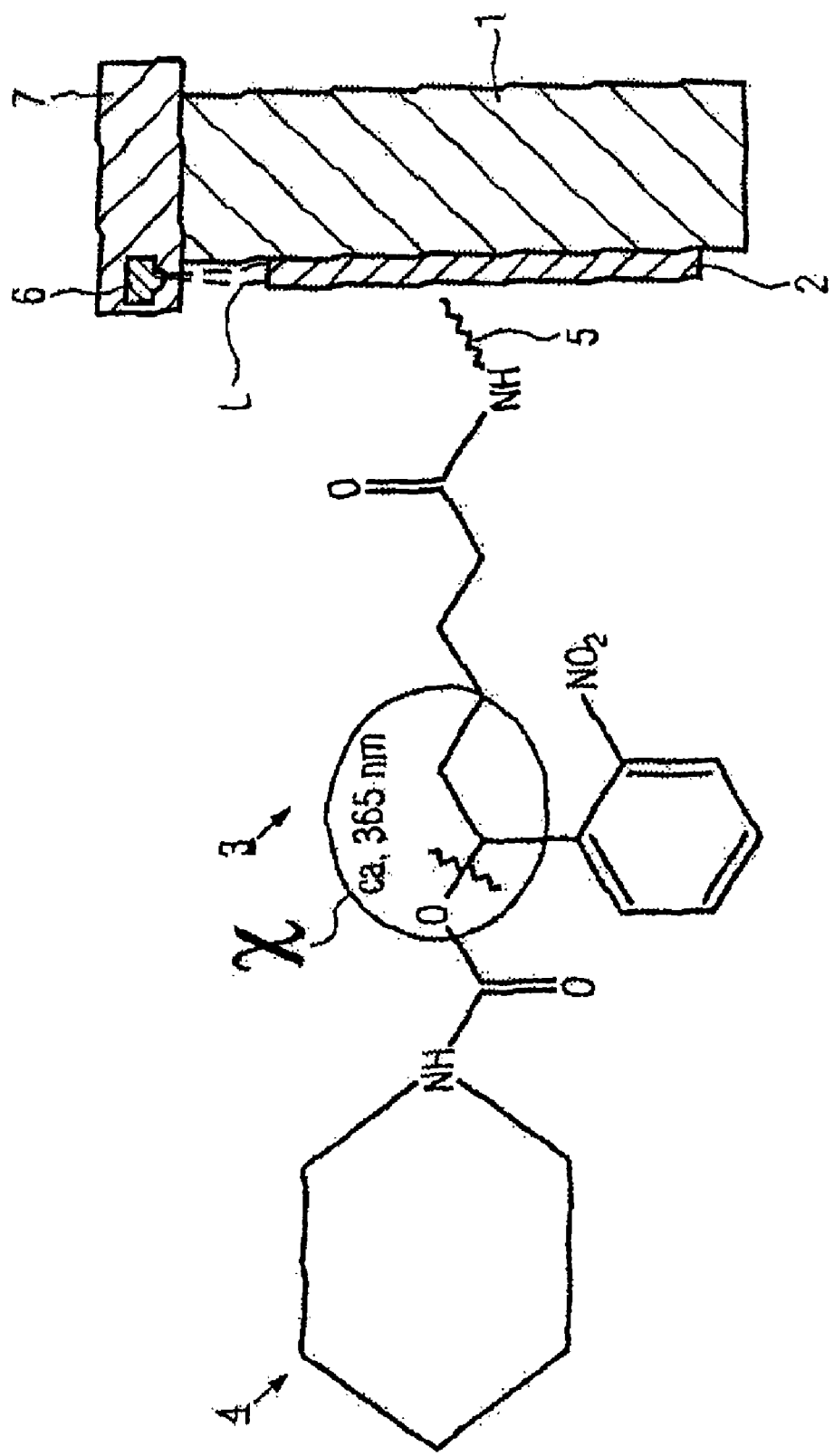
FIG. 1 shows an embodiment of the transdermal therapeutic system for optically
  i. controlled active-ingredient dosage.

The transdermal therapeutic system shown in FIG. 1 comprises a carrier material 1, wherein the carrier material is formed as a patch, bandage, wound dressing, or the like. This facilitates application to the skin.

A (partial) polymer coating 2 is arranged on the carrier material 1 as a waveguide. The present transdermal therapeutic system, i.e. the patch or the wound bandage or the wound dressing, is thus formed with an (ideally air-permeable) polymer layer or with a mesh of polymer fibers configured as optical waveguides 2.

Photolabile linkers 3 are immobilized on this optical waveguide 2, i.e. on the polymer surface, the active ingredient 4, in turn, being bound to the linkers.

DETAILED DESCRIPTION

The photolinkers consists of two functional groups that serve to establish the bond with the active ingredient and the bond with the waveguide surface. A possible immobilization strategy is the modification of the surface, i.e. by a wet-chemical process or by plasma treatment, to produce functional groups thereon. For instance (primary) amino or hydroxy groups are suited for this. If the linker molecule is provided with an (active) ester (e.g. N-hydrosuccinimide ester) or if it is activated for example with EDC, it can react with the amino or hydroxy groups on the waveguide surface to form carboxylic acid amide and ester, respectively. Hence, the linker molecule is covalently anchored to the surface. Likewise, the active ingredient molecule must be provided with the linker. To this end similar chemical reactions can here be carried out as on the waveguide surface. Ring formation on the surface and polymerization, respectively, must be prevented through a protective group strategy, if necessary. Apart from the two functional groups for reaction with the active ingredient molecule and with the surface, the molecule must have a photolabile bond to release the active ingredient. In the reaction between active ingredient molecule and photolinker, attention must be paid that upon release a possible residue of the photolinker on the active ingredient molecule shows no disadvantageous behavior in its effect (effect and side-effect).

The structure of the photolabile linker 3 is only shown by way of example in FIG. 1, where the immobilization of the photolabile linker 3 on the polymer surface is symbolically illustrated with a wavy line 5.

Likewise, the active ingredient (medicament) 4 is just outlined symbolically via a hexagon; a specific structure of the active ingredient shall not be predetermined thereby.

The photolabile linker 3 can be cleaved by light pulses L in the waveguide 2. This process is outlined in the circle designated by X for an exemplary wavelength in the UV light range of $\lambda=365$ nm through the further wave line. Hence, the transdermal therapeutic system releases the active ingredient 4 upon cleavage of the photolabile linker 3.

The light pulse L is generated by means of the light source 6 and coupled via an optical device into the optical waveguide 2.

The light source 6 is controlled via the electronic system 7.

However, it is also possible in a further embodiment to form the optical waveguide at least sectionwise as a photonic crystal, the light source being then integratable into the region of the photonic crystal. The photonic crystal enables a filtering of the broad-band radiation, which is e.g. emitted by thermal radiation. A separate optical system for coupling in the radiation is not required in this embodiment.

Likewise, it is also possible to provide an electrically conductive and/or magnetic metal in a portion of the photonic crystal, the metal being heatable by the action of an electric and/or magnetic field. It is thereby possible to integrally form the light source in the waveguide. Moreover, the coupling of light into the waveguide can then be omitted altogether.

Light waves L coupled into the waveguide 2 (or generated therein as has been explained above) produce an evanescent field in the environment of the optical waveguide 2. The photolabile linker 3 is cleaved by the action of the evanescent field produced by light pulses in the optical waveguide, thereby releasing the active ingredient, which offers a considerable advantage over a merely continuous release.

There are photolabile linkers (also called photosensitive linkers) for a wide wavelength range, both in the visible light and in the UV-light range. A possible light source 6 for the use of the transdermal therapeutic system would therefore be offered by commercially available UV-LEDs, e.g. in the range of $\lambda=365$ nm, as outlined in FIG. 1.

Figure 2A:
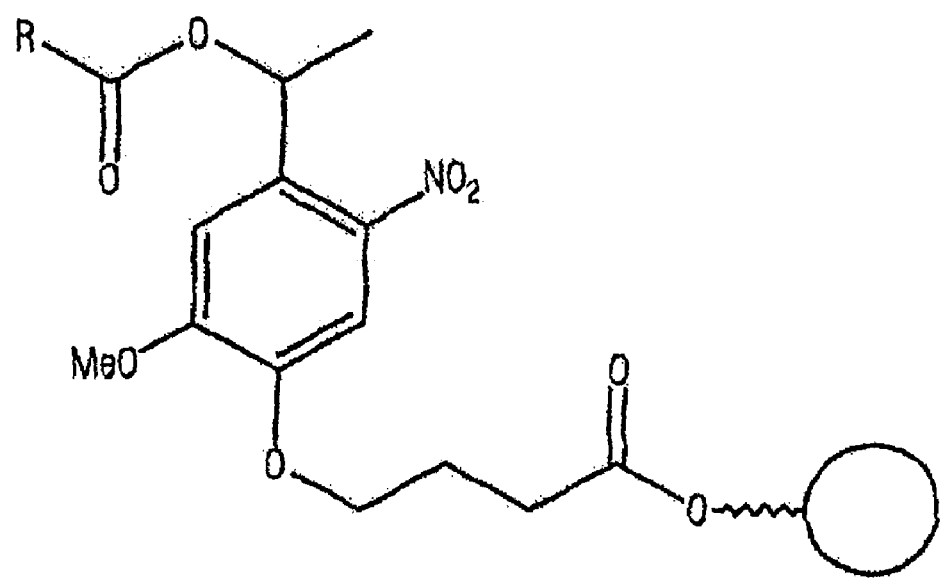
FIG. 2A shows an embodiment of a photolabile linker in the UV spectrum.
Figure 2B:
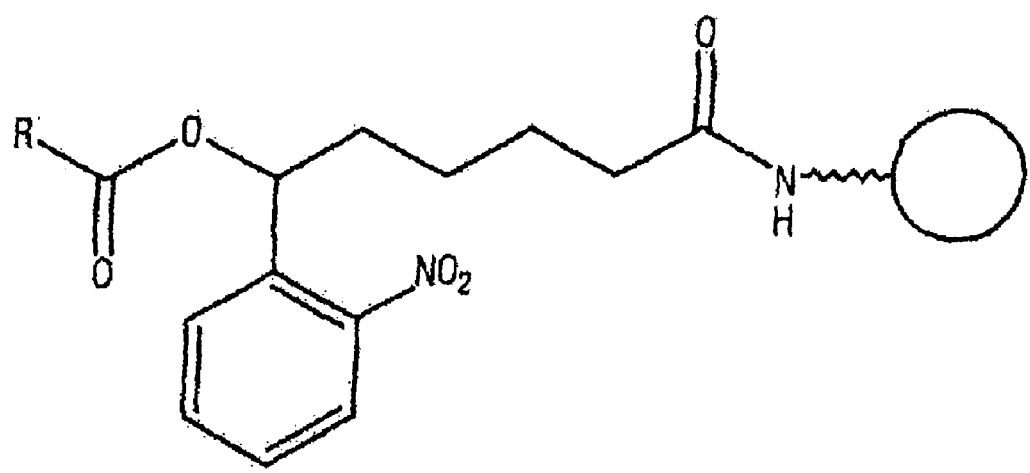
FIG. 2B shows a further embodiment of a photolabile linker in the UV spectrum;
  i.

In this wavelength range there exist suitable photolabile linkers, of which two are shown in FIGS. 2A and 2B by way of example. A list of various photosensitive linkers that can be used in the present invention is given in Bannwarth, W., Hinzen, B., Combinatorial Chemistry, Vol. 25, Wiley-VCH.

The transdermal therapeutic system as described herein is thus based on the cleavage of the photolabile linkers in the evanescent field of the optical waveguide, which enables the use of UV light without damage to the patient's skin because the light power in the evanescent filed can be kept low. Moreover, when UV light is used, the photolabile linker need not be shielded against daylight. Since wound bandages or also patches are normally exposed to visible light at least temporarily, such a shield would be required if wavelength ranges of the visible light were used. Consequently, the use of UV light permits an unproblematic application of the transdermal therapeutic system also in daylight. At the same time the use of UV light prevents the propagation of germs, or the like, on the polymer surface owing to the antimicrobial action thereof, whereby the risk of allergies or infections is additionally reduced.

In contrast to the above-described electrochemically-based controllable transdermal therapeutic system, also uncharged molecules can be used in the transdermal therapeutic system described herein with optically controlled active-ingredient dosage, whereby the range of application of this transdermal therapeutic system is increased considerably.

Since with a direct immobilization of the active ingredient via neutral photolabile linkers an adhesive layer between carrier material and active ingredient can be dispensed with, the risk of a contact allergy in the patient is minimized.

An optically based control system additionally offers the possibility of determining the real dose of released active ingredient through corresponding sensors and of directly intervening in the further therapy, if necessary, after the data have been transmitted to the attending physician. One possibility of detecting the effectively released active-ingredient dose by integration of corresponding sensors is the measurement of the extinction of the light in the optical waveguide in response to the surface covering density by means of a diode array.

Possible fields of application of the present transdermal therapeutic system are the therapy of chronic wounds or chemotherapy.

Figure 3:
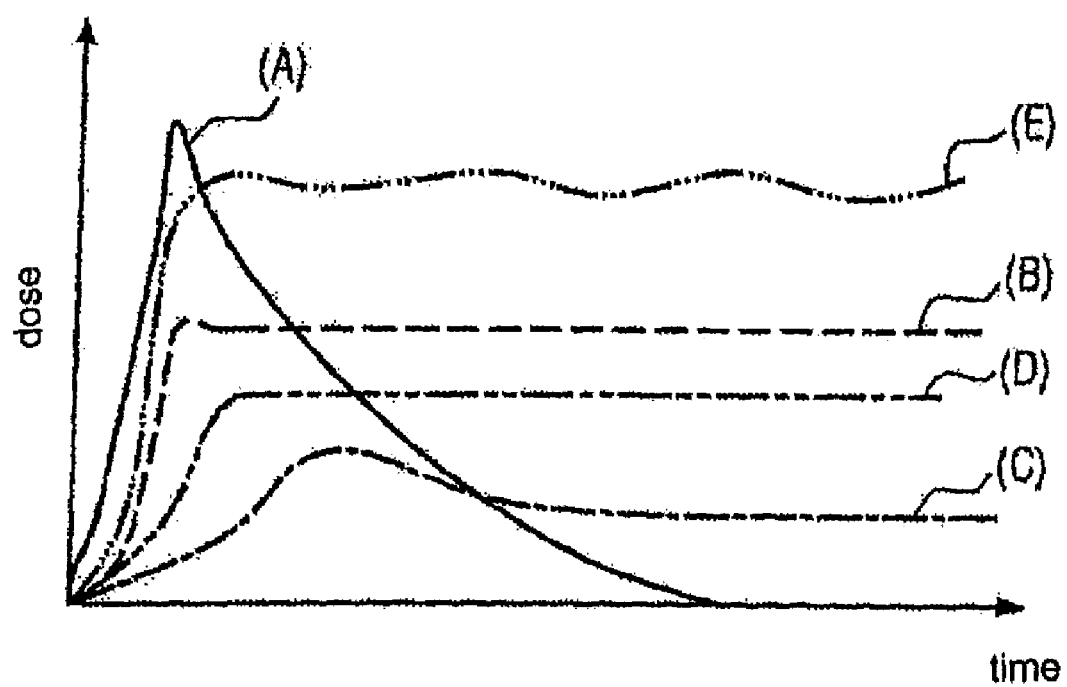
FIG. 3 shows a time curve of the active ingredient dosage with different forms of
  i. administration, including the optically controlled active-ingredient dosage in the present transdermal therapeutic system.

A comparison of the time curve of the active ingredient release in the case of different forms of administration is shown in FIG. 3. In FIG. 3, the corresponding dose of active ingredient is plotted over time.

Here curve A (continuous line) shows the active ingredient distribution for an administration by way of injection or a tablet. The rapid rise in the amount of active ingredient and the subsequent, also rapid, drop in the dose of active ingredient is clearly visible.

Curve B (broken line) shows the distribution of the active ingredient dose over time for a passive transdermal therapeutic system, wherein the rapid rise in combination with the time-constant active-ingredient release becomes apparent.

Curves C, D and E (dash-dotted lines) show individual active-ingredient dose deliveries with the present transdermal therapeutic system. The adaptivity of the amount of the active-ingredient dose delivery over time becomes thereby apparent.

In the present embodiments an immobilization of photolabile linkers is possible over a wide wavelength spectrum, and a special advantage of the use of a UV light source is here the unproblematic application of the transdermal therapeutic system in daylight. Furthermore, an exploitation of the antimicrobial action of the UV light is also possible.

Apart from a polymer fiber or a network/mesh of polymer fibers, a planar carrier film into which light is coupled in a corresponding way is also possible as a "substrate" for the photolabile linker.

Apart from this, organic semiconductive polymers can also be used. These are employed for making OLEDs (organic light-emitting diodes). A structure consisting of a plurality of organic layers is here in particular possible.

A composite of polymer fibers is advantageous insofar as the enlarged surface entails a higher active-ingredient capacity.

Two possible photolabile linkers are shown in FIGS. 2A and 2B. In principle, however, a great number of possible photolabile linkers are available, also for wavelengths other than the one specified in the instant case.

We claim:

1. A transdermal therapeutic system for the controllable release of an active ingredient, comprising at least one waveguide configured as an optical waveguide, wherein the active ingredient is detachably deposited on the optical waveguide via a photolabile linker molecule that is immobilized on the waveguide and cleavable from the active ingredient by the action of an evanescent field produced by light pulses in the optical waveguide.

2. The transdermal therapeutic system according to claim 1, wherein the waveguide is configured as at least a polymer fiber or as a polymer fiber composite.

3. The transdermal therapeutic system according to claim 1, wherein the waveguide is formed as a polymer layer, particularly as a planar carrier film.

4. The transdermal therapeutic system according to claim 3, wherein the polymer layer is air-permeable.

5. The transdermal therapeutic system according to claim 1, comprising use of light in the visible or ultraviolet wavelength range or infrared light.

6. The transdermal therapeutic system according to claim 1, wherein an optically based control system controls the generation of the electromagnetic pulses by the dosed release of the active ingredient.

7. The transdermal therapeutic system according to claim 6, including a light source for generating light pulses.

8. The transdermal therapeutic system according to claim 1, including an optical system for coupling the electromagnetic pulses into the waveguide.

9. The transdermal therapeutic system according to claim 1, wherein the transdermal therapeutic system is subdivided into segments, the individual segments being sequentially activatable for a dosed release of the active ingredient.

10. The transdermal therapeutic system according to claim 9, including a sensor for determining a dose of released active ingredient.

11. The transdermal therapeutic system according to claim 10, including a diode or a diode array for measuring extinction in dependence upon the surface covering density for determining the dose of released active ingredient.

12. The transdermal therapeutic system according to claim 1, including a carrier layer on which the waveguide is arranged.

13. The transdermal system according to claim 12, wherein the carrier layer is formed as a patch, a wound dressing or a wound bandage.

14. A transdermal therapeutic system for the controllable release of an active ingredient, comprising at least one waveguide, wherein the active ingredient is detachably deposited on the waveguide via a bond which is cleavable by electromagnetic pulses in the waveguide which is configured as an optical waveguide, with said cleavable bond being a photolabile linker molecule which is immobilized on the waveguide and cleavable from the active ingredient by the action of an evanescent field produced by light pulses in the optical waveguide.

15. The transdermal therapeutic system according to claim 14, wherein an optically based control system controls the generation of the electromagnetic pulses by the dosed release of the active ingredient.

16. The transdermal therapeutic system according to claim 15, wherein the optical system couples the electromagnetic pulses into the waveguide.

17. The transdermal therapeutic system according to claim 14, wherein the transdermal therapeutic system is subdivided into segments, the individual segments being sequentially activatable for a dosed release of the active ingredient.

18. The transdermal therapeutic system according to claim 17, including a sensor for determining a dose of released active ingredient.

19. The transdermal therapeutic system according to claim 14, including a carrier layer on which the waveguide is arranged.

20. The transdermal system according to claim 19, wherein the carrier layer is formed as a patch, a wound dressing or a wound bandage.

21. A transdermal therapeutic system for the controllable release of an active ingredient, comprising at least one waveguide, wherein the active ingredient is detachably deposited on the waveguide via a bond which is cleavable by electromagnetic pulses in the waveguide which is configured as an optical waveguide, a carrier layer on which the waveguide is arranged, the carrier layer is formed as a patch, a wound dressing or a wound bandage, with said cleavable bond being a photolabile link linker molecule which is immobilized on the waveguide and cleavable from the active ingredient by the action of an evanescent field produced by light pulses in the optical waveguide.

22. The transdermal therapeutic system according to claim 21, including an optically based control system for controlling the generation of the electromagnetic pulses by the dosed release of the active ingredient.

23. The transdermal therapeutic system according to claim 22, wherein the optical system couples the electromagnetic pulses into the waveguide.

24. The transdermal therapeutic system according to claim 23, wherein the transdermal therapeutic system is subdivided into segments, the individual segments being sequentially activatable for a dosed release of the active ingredient.

25. The transdermal therapeutic system according to claim 24, including a sensor for determining a dose of released active ingredient.

26. The transdermal therapeutic system according to claim 25, including a diode or a diode array for measuring extinction in dependence upon the surface covering density for determining the dose of released active ingredient.

* * * * *